US010478615B2

(12) United States Patent
Tol et al.

(10) Patent No.: US 10,478,615 B2
(45) Date of Patent: Nov. 19, 2019

(54) IMPLANTABLE MEDICAL SYSTEM

(75) Inventors: Jeroen Jacob Arnold Tol, Eindhoven (NL); Ke Wang, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 446 days.

(21) Appl. No.: 13/128,311

(22) PCT Filed: Nov. 4, 2009

(86) PCT No.: PCT/IB2009/054894
§ 371 (c)(1),
(2), (4) Date: May 9, 2011

(87) PCT Pub. No.: WO2010/055442
PCT Pub. Date: May 20, 2010

(65) Prior Publication Data
US 2011/0224766 A1 Sep. 15, 2011

(30) Foreign Application Priority Data
Nov. 14, 2008 (EP) .................................... 08169166
Jan. 23, 2009 (EP) .................................... 09151234

(51) Int. Cl.
*A61N 1/36* (2006.01)
*A61N 1/05* (2006.01)
(52) U.S. Cl.
CPC ................... *A61N 1/0534* (2013.01)
(58) Field of Classification Search
CPC ............................. A61N 1/3718; A61N 1/37
USPC ....................................................... 607/116
See application file for complete search history.

(56) References Cited

U.S. PATENT DOCUMENTS 7,190,569 B2    3/2007  O'Phelan
7,844,344 B2 *  11/2010 Wahlstrand .......... A61N 1/0534
                                                         607/116
2002/0116028 A1* 8/2002  Greatbatch ............ A61N 1/056
                                                         607/9

(Continued)

FOREIGN PATENT DOCUMENTS

WO    2007047966 A2    4/2007
WO    2008051913 A1    5/2008

OTHER PUBLICATIONS

International Search Report from International Application No. PCT/IB2009/054894, dated Feb. 5, 2010, 8 pp.

(Continued)

*Primary Examiner* — Michael J D Abreu
(74) *Attorney, Agent, or Firm* — Shumaker & Sieffert, P.A.

(57) ABSTRACT

This invention relates to an implantable medical system, where an implantable device including a power source operable connected to electrical components is adapted to generate electrical pulses, and a probe having a distal-end and a proximal-end. The distal-end has one or more electrodes adapted to be in electrical contact with a target tissue and wires for connecting the one or more electrodes to the implantable device. The wires conduct the electrical pulses from the implantable device to the one or more electrodes and into the target tissue. The probe has at least one capacitor and wires for connecting the at least one capacitor to the electrical components in the implantable device such that the at least one capacitor forms a part of the electrical components of the implantable device.

36 Claims, 5 Drawing Sheets

(56) References Cited

U.S. PATENT DOCUMENTS

| | | | |
|---|---|---|---|
| 2006/0271138 A1* | 11/2006 | MacDonald | A61N 1/056 607/119 |
| 2007/0112398 A1* | 5/2007 | Stevenson | A61N 1/05 607/63 |
| 2008/0154348 A1* | 6/2008 | Atalar et al. | 607/116 |
| 2008/0161886 A1 | 7/2008 | Stevenson | |
| 2008/0161887 A1 | 7/2008 | Hagen | |
| 2009/0088812 A1* | 4/2009 | Wulfman | A61N 1/056 607/9 |
| 2010/0174349 A1* | 7/2010 | Stevenson | A61N 1/05 607/116 |

OTHER PUBLICATIONS

International Preliminary Report from International Application No. PCT/IB2009/054894, dated May 17, 2011, 6 pp.
Communication pursuant to Article 94(3) EPC from counterpart European Application No. 09759797.5, dated Jul. 22, 2013, 4 pp.
Response to Communication dated Jul. 22, 2013, from counterpart European Application No. 09759797.5, filed on Nov. 29, 2013, 9 pp.
Communication pursuant to Article 94(3) EPC from counterpart European Application No. 09759797.5, dated Apr. 13, 2015, 4 pp.
Response to Communication dated Apr. 13, 2015, from counterpart European Application No. 09759797.5, filed on Aug. 13, 2015, 13 pp.
Response to Communication dated Apr. 13, 2015, from counterpart European Application No. 09759797.5, filed on Aug. 14, 2015, 13 pp.
Intention to Grant from counterpart European Application No. 09759797.5, dated Jun. 3, 2016, 44 pp.

* cited by examiner

IMPLANTABLE MEDICAL SYSTEM

FIELD OF THE INVENTION

The present invention relates to an implantable medical system and to a probe adapted to be connected to an implantable device comprised in the implantable medical system.

BACKGROUND OF THE INVENTION

Deep brain stimulation (DBS) is used to treat a variety of disabling neurological symptoms, e.g. symptoms of Parkinson's disease (PD), such as tremor, rigidity, stiffness, slowed movement, and walking problems. The procedure is also used to treat essential tremor, a common neurological movement disorder.

In DBS, a long thin probe, 8-10 cm long, is planted deep within the brain, through a burrhole in the top of the skull. The distal end of the probe contains electrodes and is positioned within the targeted brain. These electrodes are connected by a cable to an implantable device with electrical components and a battery. This implantable device contains capacitors, which might be needed for capacitive voltage conversion of the battery voltage into a programmable lower or higher voltage needed to generate electrical pulses. Once the probe and implantable device is in place, the electrical pulses are sent from the implantable device to the electrodes into the targeted brain tissue. These current pulses interfere with the neural activity of the targeted brain tissue, which leads to a reduction or even an elimination of tremor and PD symptoms.

The problem with current DBS systems and other similar systems such as heart pacemaker systems is that the electrical components include various bulky capacitors for a.o. voltage conversion, levels shifters, charge balancing and frequency tuning. In case of DBS systems, the implantable device contains electrical components and a battery. The capacitors in the implantable device consume precious space in the implantable, which effectively reduce the size of the (rechargeable) battery and/or the available functionality of the DBS stimulator.

SUMMARY OF THE INVENTION

The object of the present invention is to improve prior art implantable medical systems by making them among other things more compact and user friendly.

According to the first aspect, the present invention relates to an implantable medical system, comprising:

an implantable device comprising a power source operable connected to electrical components adapted to generate electrical pulses, and a probe having a distal-end and a proximal-end, the distal-end comprising one or more electrodes adapted to be in electrical contact with a target tissue and wires for connecting the one or more electrodes to the implantable device, where the wires conduct the electrical pulses from the implantable device to the one or more electrodes and into the target tissue, wherein the probe comprises at least one capacitor and wires for connecting the at least one capacitor to the electrical components comprised in the implantable device such that the at least one capacitor forms a part of the electrical components of the implantable device.

Therefore, some or all of the capacitors that are needed to perform various functions of the implantable device are moved from the implantable device into the probe. This means that more space is available in the implantable device for other purposes, or that the implantable device can be made smaller.

Further, the battery lifetime of the implantable medical system may be increased because by moving capacitors from the implantable device and into the probe more space will be available in the implantable device for increasing the size of the battery. Also, by making the battery larger the percentage discharge becomes smaller, assuming the time between charging and the power consumption of the device does not change. In general, the smaller the discharge levels of a battery becomes, the more often can it be charged, i.e. the number of charge cycles goes up and the same battery can be used longer before it needs to be replaced with a new one.

In one embodiment, the shape of the at least one capacitor comprised in the probe is adapted to geometrical shape of the probe. In that way, the size of the capacitor and the use of the space in the probe maximized.

In one embodiment, the electrical components comprised in the implantable device include at least one further capacitor in addition to said at least one capacitor.

In one embodiment, the geometrical shape of the probe is cylindrical.

In one embodiment, the capacitor is partitioned into multiple sub-capacitors connected in parallel and/or in series. In one embodiment, the probe is partitioned into multiple segments interlinked by a bendable separation portion, where the segments comprise at least of said sub-capacitors. Thus, the mechanical flexibility and bendability of the probe is enhanced.

In one embodiment, the capacitor is formed by layered structures comprising at least a first and a second conducting layer separated by a dielectric layer.

In one embodiment, the dielectric constant of the dielectric layer is higher than 5.

In one embodiment, the thickness of the dielectric layer is less than 25 nm.

In one embodiment, the layered structures are microstructured so as to increase the thickness of the dielectric layer.

In one embodiment, the layered structures comprise an interdigitated capacitor design so as to increase the effective surface area of the layered structures.

Accordingly, by increasing the capacitance and/or reducing the thickness of the dielectric layer and/or increase the thickness of the dielectric layer capacitance may be increased such that it contributes to the electrical components in the implantable device.

In one embodiment, the layered structures comprise a repetition of metal-dielectric-metal layers or a repetition of the interdigitated capacitor design.

In one embodiment, the capacitors are connected in parallel.

In one embodiment, the layered structure further includes an interconnect layer with said wires embedded therein for connecting the at least one capacitor and said electrical components comprised in the implantable device together.

According to a second aspect, the present invention relates to a probe adapted to connected to an implantable device, where the implantable device comprises a power source operable connected to electrical components adapted to generate electrical pulses, where the probe has a distal-end and a proximal-end, the distal-end comprising one or more electrodes adapted to be in electrical contact with a target tissue and wires extending from the one or more electrodes to the proximal-end adapted to connect the electrodes to the implantable device for conducting the electrical pulses from the implantable device to the one or more electrodes and into the target tissue, wherein the probe comprises at least one capacitor and wires extending from the at least one capacitor to the proximal-end adapted for connecting the at least one capacitor to the electrical components comprised in the implantable device such that the at least one capacitor forms a part of the electrical components of the implantable device.

The probe may be manufactured by use of standard techniques where a conducting layer and a dielectric layer are deposited alternately onto a substrate used for a probe.

The alternate deposition of the conducting layer and the dielectric layer may be repeated two or more times thus forming a multilayer capacitor.

The conducting layer may be deposited by use of physical vapor deposition. Physical vapor deposition includes, but is not limited to, such techniques as evaporation, electron beam evaporation and sputtering.

The depositing of the conducting layer may also be performed by electroplating.

The depositing of the dielectric layer may be performed by chemical or a physical vapor deposition.

The substrate may have the same geometrical shape as the probe, or it may be a flat substrate which is subsequently shaped after the deposition is completed.

The substrate may be patterned with micro or nanostructures using micro or nanofabrication techniques, such as lithography and etching.

The substrate may be coated with materials consisting of micro or nanostructures, such as nanotubes or nanoparticles.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
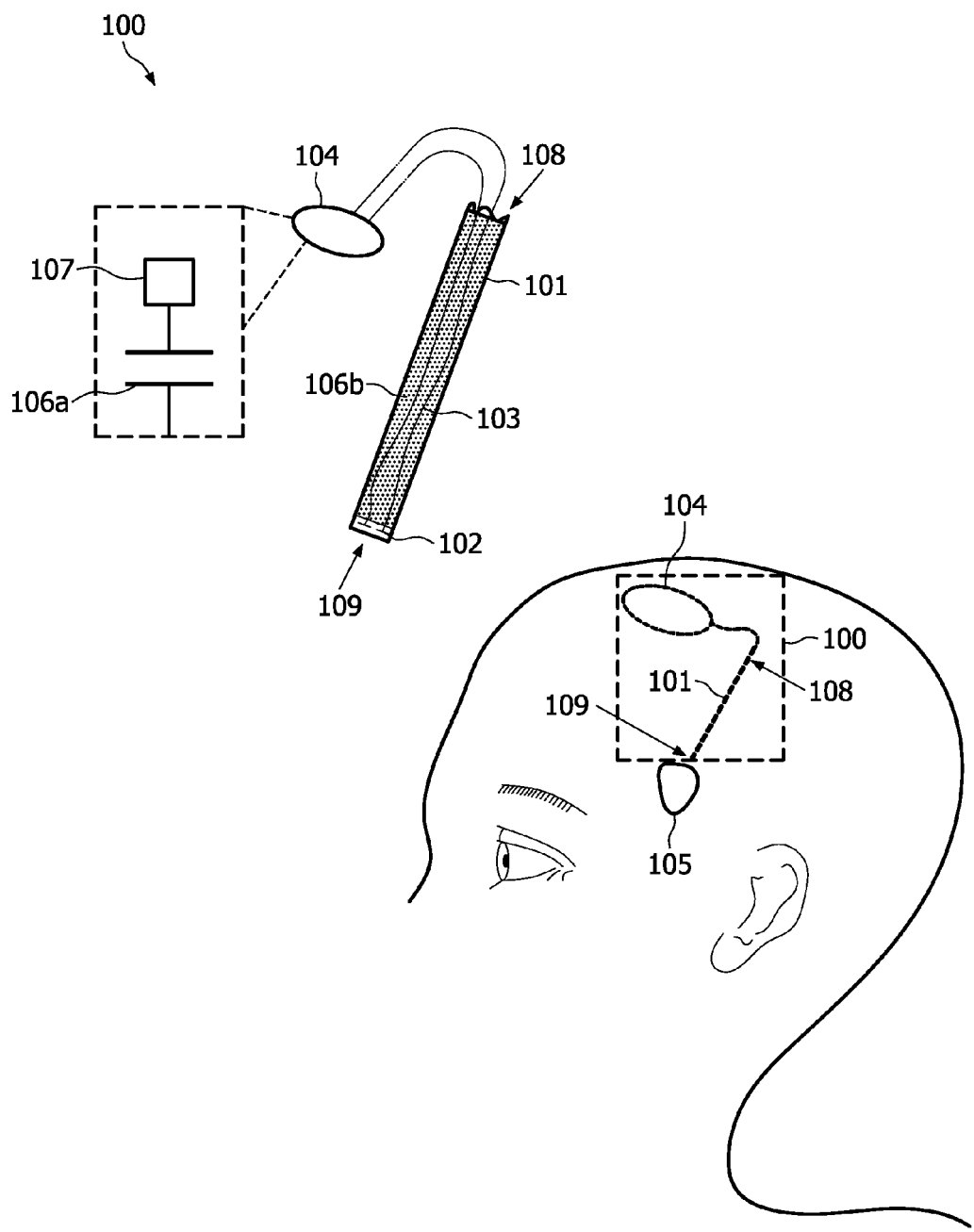
FIG. 1 shows an implantable medical system according to an embodiment of the present invention.

FIG. 1 shows an implantable medical system 100 according to an embodiment of the present invention, comprising an implantable device 104 and a probe 101. The implantable device 104 comprises a battery 107 operable connected to electrical components 106a for generating electrical pulses. The electrical components may as an example include various electronics and electronic parts, circuits, capacitors and the like. The probe 101 has a distal-end 109 and a proximal-end 108. The distal-end comprises one or more electrodes 102 adapted to be in electrical contact with a target tissue 105 and wires 103 for connecting the one or more electrodes 102 to the implantable device 104. During use, the wires conduct the electrical pulses from the implantable device 104 to the one or more electrodes 102 and into the target tissue 105. The probe 101 comprises at least one capacitor 106b and wires (not shown) for connecting the at least one capacitor 106b to the electrical components 106a comprised in the implantable device 104 such that the at least one capacitor 106b forms a part of the electrical components 106a of the implantable device 104.

It should be noted that although the capacitor 106 shown here is divided into at least one capacitor comprised in the implantable device 104 and at least one capacitor comprised in the probe 106b, the whole capacitor 106 may just as well be comprised in the probe 101.

As will be discussed in more detail in FIG. 2, the geometrical shape of the capacitor 106b is adapted to the geometrical shape of the probe 101, which may e.g. be a cylinder (having circular cross section). The probe may just as well have different cross sections, e.g. elliptical, triangular, rectangular etc.

By moving a part of (or the whole) capacitor 106b from the implantable device 104 and into the probe 101 space is freed in the implantable device, which may advantageously be used to reduce the dimensions and/or form factor of the implantable device.

The embodiment shown in FIG. 1 shows a situation where the implantable medical system 100 according to an embodiment of the present invention is used as a deep brain stimulation (DBS) device, where a long thin probe (e.g. 8-10 cm long and a diameter of 1-2 millimeters), is planted deep within the brain, through a burrhole in the top of the skull. The probe 101 has on its distal-end 109 one or more electrodes which are in direct contact with the targeted brain tissue 105. The electrodes 102 (sometimes referred to as "sites") deliver charge, supplied by the implantable device 104 to the brain tissue 105. The electrodes may be connected via a multiplexer/crosspoint switch to the electronics in the implantable device so that one can choose which electrodes provide the stimulation to the targeted brain region 105.

The capacitor 106a,b can be applied for a variety of functions, for example, in a capacitive voltage converter. The efficiency of a capacitive voltage converter goes up if the applied capacitors are made larger but this leads to reduced space for other components in the implant, including the battery. Therefore, it is advantageous to move the (larger) capacitors to the probe, because it both leads to higher conversion efficiency and the possibility to install a larger battery in the implant.

Although the medical system 100 is shown here as a DBS device, it may also be a heart pacemaker, or a spinal cord stimulator, or a bladder stimulator, or a gastric stimulator, or a medical system including the probe for stimulation and the like.

Figure 2:
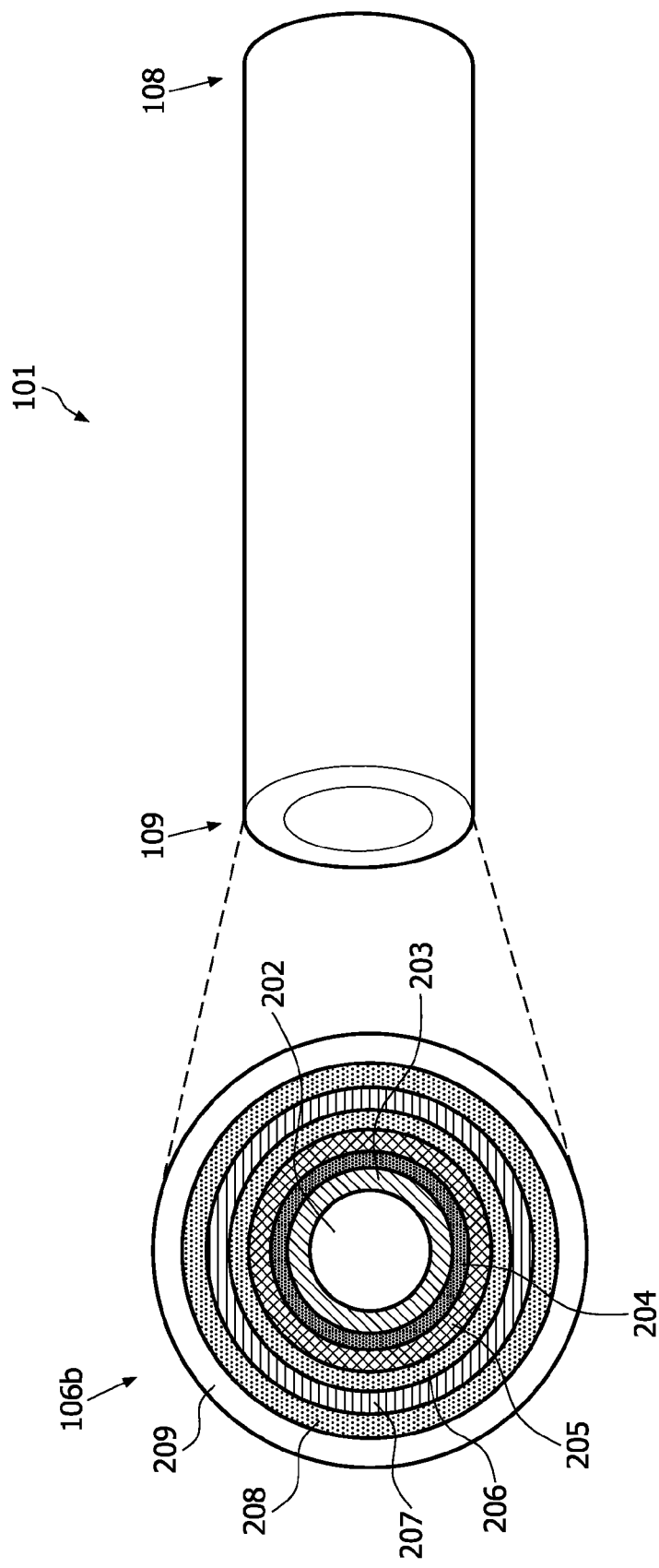
FIG. 2 shows a probe according to an embodiment of the present invention, FIG. 3a,b shows one embodiment of a probe according to an embodiment of the present invention where the probe is partitioned into multiple segments.

FIG. 2 shows a probe 101 according to an embodiment of the present invention, where the distal-end comprises said electrodes 102 electrically connected to electronics comprised in said implantable device 104 via wires 103. The electrodes are adapted to be in direct electrical contact with the target tissue 105. Either a part of the capacitor 106b or the whole capacitor 106 is embedded within the probe 101 and is adapted to be connected to said implantable device 104. The geometrical shape of the capacitor 106b is preferably adapted to the geometrical shape of the probe 101. As depicted here, since the probe has a cylindrical shape, the geometrical shape of the capacitor has also cylindrical shape.

The layered structure shown on the left side in FIG. 2 is formed by one or more layered structures comprising at least first and second conducting layers 206, 208 separated by a first dielectric layer 207. In the embodiment shown here, the outmost layer is a second dielectric layer 209, which may be of the same type as the first dielectric layer that isolates the capacitor from the target tissue 105. In this embodiment, the three inner most layers are: dielectric layer 205 which may be identical to the outermost dielectric layer, an interconnect layer 204 and a dielectric layer 203 which may be identical to the outermost dielectric layer. In one embodiment, the interconnect layer 204 comprises conductive wires embedded within the interconnect layer 204 that electrically connects the electrodes 102 to the implantable device 104. The thickness (diameter) of the wires should preferably be less than the thickness of the interconnect layer 204. Also, the interconnect layer 204 connects the capacitors internally together in the probe 101. As an example, a single integrated capacitor 106b may be split into two cylindrical parts, an upper part and a lower part. The interconnect layer 204 may then be used to connect these two parts together by e.g. connecting the second conducting layer 208 of the upper part to the first conducting layer 206 of the lower part. Other geometries of the interconnect layer are also possible. The interconnect layer could also be (partly) used as an additional conducting layer of the integrated capacitor to increase its capacitance.

The center of the probe has in this embodiment a cavity 202 which leaves space for a stiff guiding wire needed to insert the probe into the brain; this guiding is removed once the probe is in place (see FIG. 1).

Figure 3A:
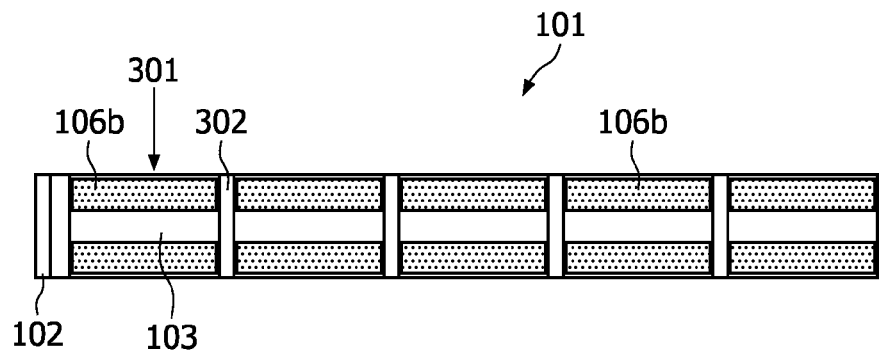
Figure 3B:
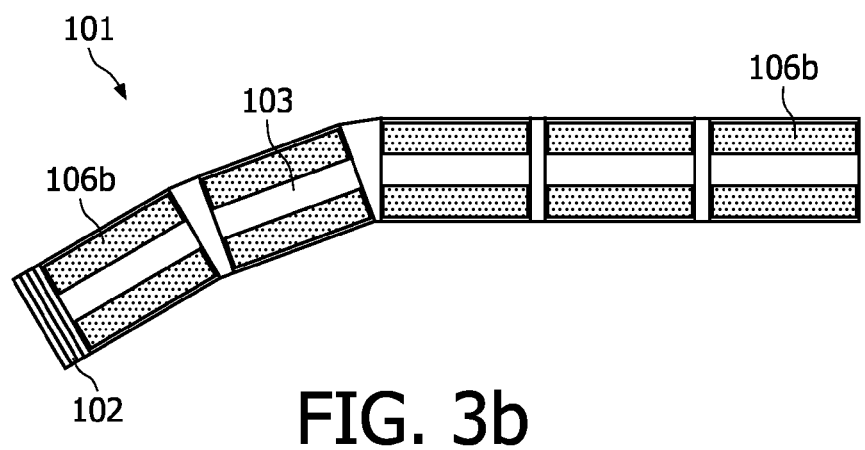

FIG. 3a,b shows one embodiment of a probe 101 according to the present invention where the probe is partitioned into multiple segments 301 interlinked by a bendable separation portion 302, which may e.g. be any type of a deformable material such as rubber, plastic and the like. The electrodes 102 are connected to said implantable device 104 by connecting wires (not shown) embedded within the interconnect layer 204 as discussed in the previous example. As depicted here, the capacitor 106b is partitioned into multiple sub-capacitors connected in parallel and/or series, where one or more sub-capacitor are embedded into each respective segment 301. As shown here, one capacitor is embedded into one segment 301. A serial connection would typically be useful if each capacitor in the series connection is individually addressable because otherwise one is simply reducing the value of the capacitance. As depicted in FIG. 3b, by partitioning the capacitor 106b and the probe in such segments/sub-capacitors the mechanical flexibility and bendability of the probe 101 comprising the capacitor 106b will be enhanced.

In one embodiment, the probe 101 comprising said capacitor 106b embedded therein may be fabricated by direct deposition of metal and dielectric layers on a substrate (not shown), where the substrate may be a cylindrical (e.g. a hollow cylinder) or a flat substrate which is subsequently bent into the final shape. For example, the substrate may already contain the interconnect layer 204 embedded in dielectrics (see FIG. 2) or the interconnect layer may also be fabricated in the same way as the other layers of the capacitor. The substrate may be rotated in an evaporator, where a thin layer of metal, e.g. gold or platinum, is evaporated around the substrate. Then, a conformal layer of e.g. parylene-C may be deposited by chemical vapor deposition. The rotational evaporation and the chemical vapor deposition step may be repeated until the final structure is achieved, e.g. the one shown in FIG. 2.

The capacitance that can be integrated in a cylindrical probe can be approximated by the equation:

$$C = \varepsilon_r \varepsilon_0 \frac{A}{d} = \varepsilon_r \varepsilon_0 \frac{\pi DL}{d}$$

where $\varepsilon_r$ is the dielectric constant of the material, d is the thickness of the dielectric layer, D is the diameter of the probe 101, L is the length of the probe 101. As an example, if D=1.27 mm, L=10 cm, $\varepsilon_r$=3 (for parylene-C), d=1 μm, then the resulting capacitance C becomes 0.01 μF.

The equation already indicates how larger capacitance can be achieved, i.e. by increasing the material's dielectric constant, reducing the thickness of the dielectric layer and/or increasing the capacitor's effective area. This is explained in more detail in the three examples below:

1. Using High $\varepsilon_r$ Dielectric:

Most biocompatible polymers have a low dielectric constant of approx 3.0. However, silicon nitride has a higher $\varepsilon_r$ (6.0-8.0). The layered structure (such as the one shown in FIG. 4) can be realized using a standard thin-film microfabrication technology. The layers can be released from e.g. a silicon wafer that after forming the layered structure is subsequently wrapped around to form said probe 101. Literature has shown that low-stress silicon nitride can survive bending in a long term without failure.

In this example, the upmost layer 401 may be parylene-C, the second layer 402 may be metal 1, the third layer 403 may be silicon nitride, the fourth layer 404 may be metal 2 (which may be identical to metal 1), the fifth layer 405 may be polyimide, and the bottom layer 406 said silicon wafer.

2. Reducing Dielectric Layer Thickness:

In addition, the dielectric layer thickness can be easily reduced using thin-film technology. Ceramic layers (such as silicon oxide) thinner than 10 nm are routinely deposited in CMOS fabrication. That already gives a 100-fold increase in the capacitance (C≈1 μF with a 10 nm-thick dielectric layer).

3. Increasing Effective Surface Area.

Figure 5:
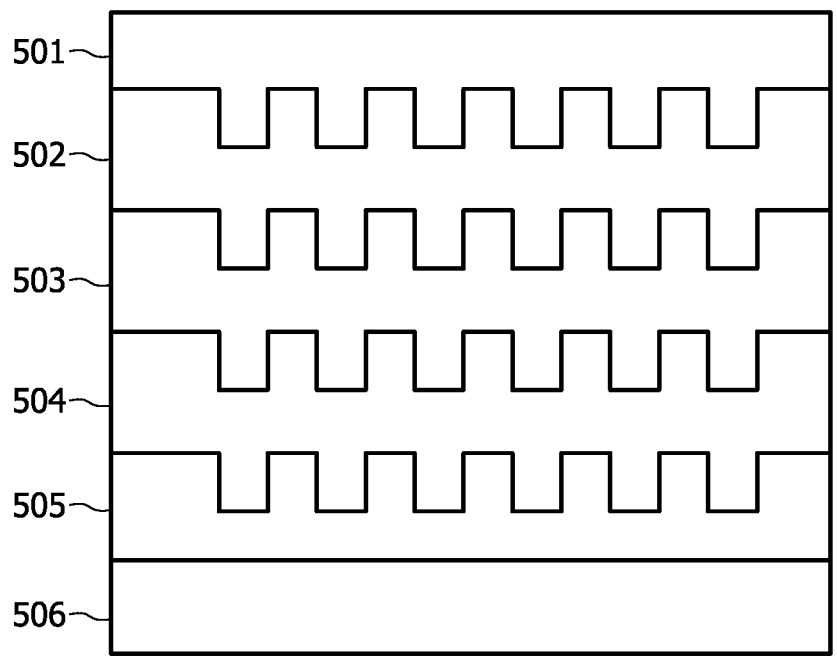
FIG. 5 shows a microstructure in a metal and dielectric layer for increasing effective surface area.

Thin-film technology can also be used to introduce microstructures in the layers and in that way increase the effective surface area. FIG. 5 shows schematically an example of such microstructures, where an increase in the effective surface area (over geometric area) of more than twofold can be achieved.

Figure 4:
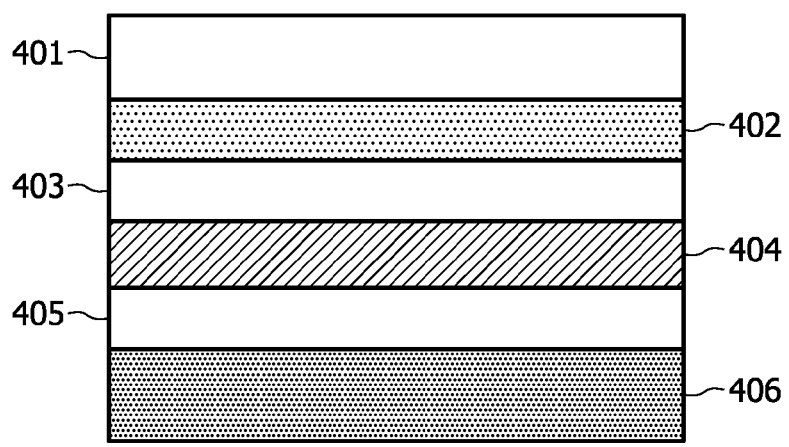
FIG. 4 shows a thin-film layer structure containing a capacitor realized from a wafer.

The arrangement of the layers in FIG. 5 is similar to the layers of FIG. 4, i.e. the upmost layer 501 may be parylene-C, the second layer 502 may be metal 1, the third layer 503 may be silicon nitride, the fourth layer 504 may be metal 2 (which may be identical to metal 1), the fifth layer 505 may be polyimide, and the bottom layer 506 a silicon wafer.

Figure 6:
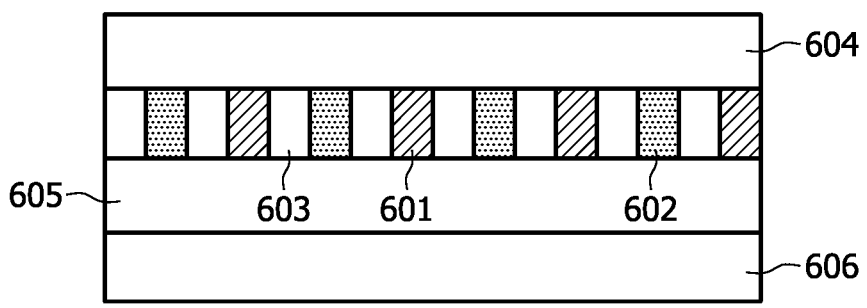
FIGS. 6 and 7 shows a cross section and an overview of an interdigitated capacitor layout.
Figure 7:
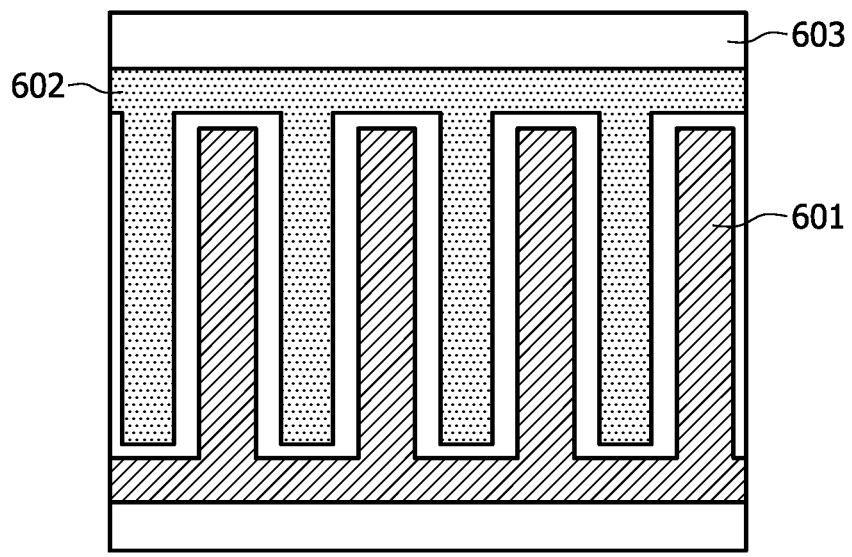

FIGS. 6 and 7 show another way to increase the effective surface area with an interdigitated capacitor layout. The interdigitated capacitor layout is shown in cross section in FIG. 6 in a top view showing its intra-metal finger structure in FIG. 7. In the embodiment shown in FIG. 6, the upmost layer 604 is a dielectric (e.g. Parylene-C), the white area portion 603 is dielectric material, the shaded portion 602 is a metal (e.g. metal 1) and the patterned portion 601 is a metal (e.g. metal 2). The bottom layer 606 may be a silicon wafer and the layer on top of that 605 may be e.g. a polyimide.

This interdigitated structure is advantageous if the intra-metal lateral capacitance has a higher specific areal capacitance than the vertical inter-metal capacitance in the chosen process technology. This occurs if the metal thickness becomes sufficiently larger than the minimum allowable spacing between two tracks in the same metal layer.

Figure 8:
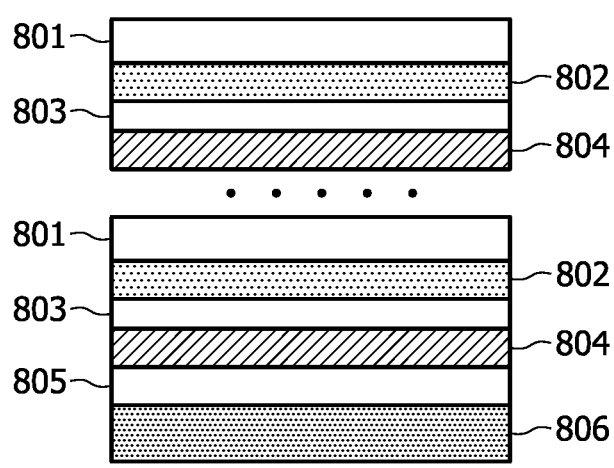
FIG. 8 shows a stacked sandwich structure to create multiple capacitors in parallel.

FIG. 8 shows a stacked sandwich structure to create multiple capacitors in parallel, showing a repetition of metal layers 802, 804 separated by a dielectric layer 803. The top layer is preferably dielectric layer 801, the bottom layer may e.g. be a silicon wafer 806, and on top of that e.g. a polyimide layer 805.

Certain specific details of the disclosed embodiments are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. An implantable medical system, comprising:
an implantable device comprising a power source and electrical components, the power source and electrical components configured to generate electrical pulses; and
a probe having a distal end and a proximal end, the distal end comprising one or more electrodes configured to be in electrical contact with a target tissue, the probe comprising:
first wires connecting the one or more electrodes to the implantable device, the first wires configured to conduct, from the implantable device to the one or more electrodes and into the target tissue, the electrical pulses generated by the electrical components of the implantable device, wherein the first wires extend from the distal end of the probe to the proximal end of the probe;
at least one capacitor configured to perform one or more functions of the implantable device; and
second wires connecting the at least one capacitor to the electrical components in the implantable device such that the at least one capacitor forms a part of the electrical components of the implantable device, wherein the second wires are different than the first wires.

2. An implantable medical system according to claim 1, wherein the at least one capacitor includes a first conducting layer, a second conducting layer, and a dielectric layer separating the first and second conducting layers.

3. An implantable medical system according to claim 2, wherein the dielectric layer comprises silicon nitride and a dielectric constant of the dielectric layer is between 6.0 and 8.0.

4. An implantable medical system according to claim 2, wherein a thickness of the dielectric layer is less than 25 nanometers (nm).

5. An implantable medical system according to claim 2, wherein the first and second conducting layers are microstructured to increase an effective surface area of the at least one capacitor.

6. An implantable medical system according to claim 5, wherein the first and second conducting layers are connected in parallel.

7. An implantable medical system according to claim 2, wherein the at least one capacitor comprises an interdigitated capacitor design to increase an effective surface area of the at least one capacitor.

8. An implantable medical system according to claim 2, wherein the at least one capacitor comprises a repetition of metal-dielectric-metal layers or a repetition of an interdigitated capacitor design.

9. An implantable medical system according to claim 1, wherein the at least one capacitor has a cross sectional geometric shape similar to a cross sectional geometric shape of the probe.

10. An implantable medical system according to claim 9, wherein the probe is cylindrical and the at least one capacitor is cylindrical.

11. An implantable medical system according to claim 10, wherein the at least one capacitor is a hollow cylinder.

12. An implantable medical system according to claim 1, wherein the at least one capacitor is partitioned into multiple sub-capacitors connected in at least one of parallel or series.

13. An implantable medical system according to claim 12, wherein the probe is partitioned into multiple segments interlinked by a bendable separation portion, and wherein each segment comprises at least one sub-capacitor.

14. An implantable medical system according to claim 1, wherein the at least one capacitor includes a first capacitor, and the electrical components in the implantable device include at least one second capacitor in addition to the first capacitor.

15. An implantable medical system according to claim 1, wherein the at least one capacitor includes a film.

16. An implantable medical system according to claim 1, wherein the one or more functions of the implantable device performed by the at least one capacitor include: level shifting, charge balancing, or frequency tuning.

17. An implantable medical system according to claim 1, wherein the at least one capacitor has an outer diameter generally equal in size to an inner diameter of the probe.

18. An implantable medical system according to claim 1, wherein the one or more functions of the implantable device performed by the at least one capacitor include voltage conversion.

19. An implantable medical system according to claim 1, wherein the first wires are configured to conduct the electrical pulses directly from the implantable device to the one or more electrodes.

20. A probe configured to be connected to an implantable device having a power source and electrical components configured to generate electrical pulses, the probe comprising:
a proximal end;
a distal end comprising one or more electrodes configured to be in electrical contact with a target tissue;
first wires connecting the one or more electrodes to the implantable device, wherein the first wires are configured to conduct, directly from the implantable device and to the one or more electrodes, the electrical pulses generated by the electrical components of the implantable device;
at least one capacitor configured to perform one or more functions of the implantable device; and
second wires connecting the at least one capacitor to the implantable device, wherein the second wires are configured to connect the at least one capacitor to the electrical components of the implantable device such that the at least one capacitor forms a part of the electrical components of the implantable device, and wherein the second wires are different than the first wires.

21. A probe according to claim 20, wherein the at least one capacitor includes a first conducting layer, a second conducting layer, and a dielectric layer separating the first and second conducting layers.

22. A probe according to claim 21, wherein the dielectric layer comprises silicon nitride and a dielectric constant of the dielectric layer is between 6.0 and 8.0.

23. A probe according to claim 21, wherein a thickness of the dielectric layer is less than 25 nanometers (nm).

24. A probe according to claim 21, wherein the first and second conducting layers are microstructured to increase an effective surface area of the at least one capacitor.

25. A probe according to claim 24, wherein the first and second conducting layers are connected in parallel.

26. A probe according to claim 21, wherein the at least one capacitor comprises an interdigitated capacitor design to increase an effective surface area of the at least one capacitor.

27. A probe according to claim 21, wherein the at least one capacitor comprises a repetition of metal-dielectric-metal layers or a repetition of an interdigitated capacitor design.

28. A probe according to claim 21, wherein the at least one capacitor further includes an interconnect layer with at least one of the first wires or the second wires embedded therein.

29. A probe according to claim 20, wherein the at least one capacitor has a cross sectional geometric shape similar to a cross sectional geometric shape of the probe.

30. A probe according to claim 29, wherein the probe is cylindrical and the at least one capacitor is cylindrical.

31. A probe according to claim 30, wherein the at least one capacitor is a hollow cylinder.

32. A probe according to claim 20, wherein the at least one capacitor is partitioned into multiple sub-capacitors connected in at least one of parallel or series.

33. A probe according to claim 32, wherein the probe is partitioned into multiple segments interlinked by a bendable separation portion, and wherein each segment comprises at least one sub-capacitor.

34. A probe according to claim 20, wherein the at least one capacitor includes a film.

35. A probe according to claim 20, wherein the one or more functions of the implantable device performed by the at least one capacitor include: voltage conversion, level shifting, charge balancing, or frequency tuning.

36. A probe according to claim 20, wherein the at least one capacitor has an outer diameter generally equal in size to an inner diameter of the probe.

* * * * *